US010485863B2

(12) United States Patent
Osterhaus et al.

(10) Patent No.: US 10,485,863 B2
(45) Date of Patent: Nov. 26, 2019

(54) INFLUENZA VACCINE

(75) Inventors: Albertus D. M. E. Osterhaus, Amsterdam (NL); Bror Morein, Uppsala (SE); Karin Lövgren Bengtsson, Uppsala (SE)

(73) Assignees: Novavax AB, Uppsala (SE); Erasmus University Rotterdam Medical Center, Rotterdam (NL)

( * ) Notice: Subject to any disclaimer, the term of this patent is extended or adjusted under 35 U.S.C. 154(b) by 299 days.

(21) Appl. No.: 13/811,493

(22) PCT Filed: Jul. 25, 2011

(86) PCT No.: PCT/SE2011/050968
§ 371 (c)(1),
(2), (4) Date: Jan. 22, 2013

(87) PCT Pub. No.: WO2012/011868
PCT Pub. Date: Jan. 26, 2012

(65) Prior Publication Data
US 2013/0129770 A1     May 23, 2013

Related U.S. Application Data

(60) Provisional application No. 61/366,983, filed on Jul. 23, 2010.

(51) Int. Cl.
*A61K 39/145*    (2006.01)
*A61K 39/12*     (2006.01)
*A61K 39/00*     (2006.01)

(52) U.S. Cl.
CPC ............ *A61K 39/145* (2013.01); *A61K 39/12* (2013.01); *A61K 2039/55577* (2013.01); *A61K 2039/70* (2013.01); *C12N 2760/16111* (2013.01); *C12N 2760/16134* (2013.01)

(58) Field of Classification Search
None
See application file for complete search history.

(56) References Cited

FOREIGN PATENT DOCUMENTS

| WO | 2002/074795 A2 | 9/2002 |
| WO | 2007/022425 A2 | 2/2007 |
| WO | 2008157419 A2 | 12/2008 |
| WO | 2010/144797 A2 | 12/2010 |
| WO | 2011/126370 A1 | 10/2011 |

OTHER PUBLICATIONS

Radosevic et al. Vaccine 2008 vol. 26, pp. 3640-3646.*
A/California/09/2009 HA PubMed sequence dated 2009.*
De Wit et al., J Virology, 2005, vol. 79, pp. 12401-12407.*
Hoffmann, et al., Eight-plasmid system for rapid generation of influenza virus vaccines, Vaccine, vol. 20, Issues 25-26, Aug. 19, 2002, pp. 3165-3170.*
Hutchinson et al., Nature Communications, DOI: 10.1038/ncomms5816, Published Sep. 16, 2014.*
Madhun, et. al., Intramuscular Matrix-M-adjuvanted virosomal H5N1 vaccine induces high frequencies of multifunctional Th1 CD4 cells and strong anitbody responses in mice; Vaccine vol. 27, pp. 7367-7376; Sep. 23, 2009.
Lovgren, et al. An experimental influenza subunit vaccine (iscom): induction of protective immunity to challenge infection in mice after intranasal or subcutaneous administration; Clin.exp. Immunology vol. 82, pp. 435-439, 1990.
Bosch, et al., Recombinant Soluble, Multimeric HA and NA Exhibit Distinctive Types of Protection against Pandemic Swine—Origin 2009 A(H1N1) Influenza Virus Infection in Ferrets; Journal of Virology, vol. 84, No. 19, pp. 10366-10374,Oct. 2010.
Pushko, et.al., Recombinant H1N1 virus-like particle vaccine elicits protective immunity in ferrets against the 2009 pandemic H1N1 influenza virus; Vaccine, vol. 28, pp. 4771-4776, May 12, 2010.
De Witt, et. al., Protection of Mice against Lethal Infection with Highly Pathogenic H7N7 Influenza A Virus by Using a Recombinant Low-Pathogenicity Vaccine Strain; Journal of Virology, vol. 79, No. 19, pp. 12401-12407; Oct. 2005.
Written Opinion of the International Searching Authority and International Search Report issued in PCT/SE2011/050968; dated Nov. 14, 2011.
Extended European Search Report issued in EP Application No. 11809955.5; dated Feb. 11, 2014.
Khurana, et al., Properly Folded Bacterially Expressed H1N1 Hemmagglutinin Globular Head and Ectodomain Vaccines Protect Ferrets against H1N1 Pandemic Influenza Virus; Plos One, Jul. 2010, e11548, vol. 5, Issue 7, pp. 1-11.
An Office Action issued in corresponding Chinese Application No. 201180035658.0; Issue No. 2013103101082660; dated Nov. 5, 2013 and English translation.
Cornelissen, L.A.H.M. et al., "A Single Immunization with Soluble Recombinant Trimeric Hemagglutinin Protects Chickens against Highly Pathogenic Avian Influenza Virus H5N1," PLOS One, vol. 5, Issue 5, e10645, pp. 1-9 (May 2010).
Wang, C.-C. et al., "Glycans on influenza hemagglutinin affect receptor binding and immune response," Proceedings of the National Academy of Sciences USA, vol. 106, No. 43, pp. 18137-18142 (Oct. 27, 2009).
Fiers, W. et al., "Soluble recombinant influenza vaccines," Phil. Trans. R. Soc. Lond. B., vol. 356, pp. 1961-1963 (2001).
Hu, K.-F. et al., "Immunostimulating complexes (ISCOMs) for nasal vaccination," Advanced Drug Delivery Reviews, vol. 51, pp. 149-159 (2001).

(Continued)

*Primary Examiner* — Shanon A. Foley
*Assistant Examiner* — Myron G Hill
(74) *Attorney, Agent, or Firm* — Cooley LLP (57) ABSTRACT

The present invention relates to a composition comprising at least one ISCOM complex and at least one ectodomain from at least one hemagglutinin (HA) domain and at least one ectodomain from at least one neuraminidase (NA) domain from one or more influenza virus, wherein the extodomains represent ectodomains isolated from the influenza virus. The invention also regards a kit. The composition may be used as an immune stimulating medicine, immune modulating pharmaceutical or a vaccine e.g. against influenza for vertebrates, e.g. birds and mammals.

20 Claims, 6 Drawing Sheets
(6 of 6 Drawing Sheet(s) Filed in Color)

(56) References Cited

OTHER PUBLICATIONS

Chen, Z. et al., "Enhanced protection against a lethal influenza virus challenge by immunization with both hemagglutinin- and neuraminidase-expressing DNAs," Vaccine, vol. 17, pp. 653-659 (1999).

Johansson, B.E., "Immunization with influenza A virus hemagglutinin and neuraminidase produced in recombinant baculovirus results in a balanced and broadened immune response superior to conventional vaccine," Vaccine, vol. 17, pp. 2073-2080 (1999).

Johansson, B.E. et al., "Dissociation of influenza virus hemagglutinin and neuraminidase eliminates their intravirionic antigenic competition," J. Virol., vol. 67, No. 10, pp. 5721-5723 (1993).

Rimmelzwaan, et al., A randomized, double blind study in young healthy adults comparing cell mediated and humoral immune responses induced by influenza ISCOM vaccines and conventional vaccines; Vaccine, 2001, vol. 19, pp. 1180-1187, Elsevier Science Limited.

\* cited by examiner

INFLUENZA VACCINE

This application claims the benefit of U.S. Provisional Application No. 61/366,983, filed Jul. 23, 2010.

The present invention relates to a composition comprising at least one ISCOM complex and at least one ectodomain from at least one hemagglutinin (HA) domain and at least one ectodomain from at least one neuraminidase (NA) domain from one or more influenza virus, wherein the extodomains represent ectodomains isolated from the influenza virus. The invention also regards a kit. The composition may be used as an immune stimulating medicine, immune modulating pharmaceutical or a vaccine e.g. against influenza for vertebrates, e.g. birds and mammals.

BACKGROUND ART

The recent emergence of the pandemic swine-origin 2009 A(H1N1) influenza virus strongly emphasises the potential of influenza viruses to cause morbidity and mortality in the human population on a global scale. Worldwide over 200 countries and overseas territories or communities have reported laboratory-confirmed cases of the pandemic virus including more than 16,000 deaths [1]. Vaccination is the primary method to prevent or lower the burden of influenza disease. However, as illustrated again by the 2009 pandemic, a rapid response during the early phase of an outbreak is hampered by the time-consuming vaccine strain preparation and vaccine manufacturing process currently used. This, combined with the notorious capacity of influenza viruses to escape from existing immunity by antigenic drift and shift, stresses the need for novel, safe and preferably broadly effective vaccines that can be produced rapidly and in flexible response to newly emerging antigenic variants.

The currently licensed influenza virus vaccines are composed of the viral envelope glycoproteins, the hemagglutinin (HA) and neuraminidase (NA). Antibodies elicited by these two large glycoproteins have distinct properties in immunity against influenza virus. Antibodies to HA generally neutralise viral infectivity by interference with virus binding to sialic acid receptors on the target cells or, subsequently, by preventing the fusion of the viral and cellular membrane through which the viral genome gains access to the target cell. Antibodies to NA disable release of progeny virus from infected cells by inhibiting the NA-associated receptor destroying enzymatic activity. The HA-mediated humoral immunity has been characterised most extensively and shown to prevent virus infection. The contribution of NA antibodies to preventing disease has been studied less well. They appeared to produce a kind of permissive immunity [2] characterised by a decrease in infectious virus release from apical surfaces of infected epithelia [2-8], reducing the probability of virus shedding and spread into the environment.

Immunisation with the combination of HA and NA provides enhanced protection against influenza [5, 9, 10]. Although HA and NA are equivalently immunogenic [2], the humoral immune response towards conventional inactivated vaccines or virus infection is naturally skewed towards HA since HA and NA occur on the viral surface at an approximately 4:1 ratio [11]. In addition, in intact virions the HA immunologically outcompetes NA in B and T cell priming as shown in mice [12]. This antigenic competition is not seen in vaccinated animals when HA and NA are administered separately [10, 13]. The currently licensed pandemic vaccines as well as the seasonal trivalent vaccines are generally prepared from whole viruses and are hence biased to contain more HA than NA antigen. Adapting the HA-NA ratio in vaccine formulations in favour of NA may provide a more balanced humoral immune response resulting in higher NA antibody levels and increased protection against disease [3, 14].

Since the current inactivated influenza virus vaccines are standardised only for the amount of HA, the NA content is variable as is, consequently, the frequency and level of seroconversion to NA, which is often rather poor [28, 29].

Typical for influenza A viruses, antigenic variants of HA and NA within a certain virus subtype able to escape from existing immunity are gradually selected in the human population. This process of antigenic drift calls for the almost annual adjustment of the seasonal vaccine composition in response to newly arising variants. In view of the threat of future influenza pandemics, caused for instance by an avian H5N1 virus, there is a need for vaccines inducing broadly protective immunity.

SUMMARY OF THE INVENTION

The present invention relates to a composition comprising at least one ISCOM complex and at least one ectodomain from at least one hemagglutinin (HA) domain and at least one ectodomain from at least one neuraminidase (NA) domain from one or more influenza virus, wherein the extodomains represent ectodomains isolated from the influenza virus, and a kit.

Compositions comprising ISCOM adjuvant and HA and NA or fragments thereof are known e.g. through WO 2008157419 and [5,9,10]. It has however not been disclosed before to use ectodomains from both HA and NA together with ISCOM adjuvant.

It has now turned out that vaccination with ectodomains from both NA and HA adjuvanted with ISCOM or ISCOM matrix reduced virus replication—e.g. by lowering pulmonary titers-, and decreased the clinical effects of infection such as body weight loss and lung pathology.

Multimeric HA and NA ectodomains have great vaccine potential, as these can be easily, rapidly, flexibly and safely produced in high quantities. The inclusion of NA in influenza vaccines, profoundly and specifically contributes to protection by HA. Its inclusion in a vaccine is likely to reduce the HA dose required and to broaden the protective immunity.

FIGURE LEGENDS

The patent or application file contains at least one drawing executed in color. Copies of this patent or patent application publication with color drawing(s) will be provided by the Office upon request and payment of the necessary fee.

FIG. 1

Design and Expression of Soluble, Multimeric HA (sHA) And NA (sNA) Proteins of 2009 A(H1N1) Influenza Virus.

A) Schematic representation of the recombinantly expressed sHA and sNA protein constructs. sHA: the HA ectodomain (a.a. 17-522) is expressed with an N-terminal CD5 signal peptide and a C-terminal trimerisation (GCN4-pII) GCN4 domain and Strep-Tag (ST), respectively. sNA: the NA head domain (a.a. 75-469) is expressed with an N-terminal CD5 signal peptide, a OneSTrEP(OS) peptide and a tetramerisation (GCN4-pLI) GCN4 domain. (B) Coomassie blue stained reducing SDS-PAGE of affinity-purified sHA and sNA proteins.

FIG. 2

Antibody Response to Vaccination with Multimeric 2009 A(H1N1) Influenza Virus HA and NA Antigens.

Ferrets were immunised on day 0 and day 20 with: 3.75 μg sHA$_3$+3.75 μg sNA$_4$ (sHA+sNA); 3.75 μg sHA$_3$ in adjuvant (ISCOM Matrix M [IMM]; sHA+IMM); 3.75 μg sNA$_4$ in adjuvant (sNA+IMM); 3.75 μg sHA$_3$+3.75 μg sNA$_4$ in adjuvant (sHA+sNA+IMM), PBS or IMM, as indicated. The antibody response to the 2009 A(H1N1) influenza virus was evaluated by hemagglutination inhibition (HI; upper panel), virus neutralisation (VN; second panel from the top) and neuraminidase inhibition (NI) assays (lower panels). Each dot represents the result of one ferret. Horizontal lines represent means. The horizontal grey bar indicates the detection limit of the assay.

FIG. 3

Clinical Effects after Challenge Inoculation with 2009 A(H1N1) Influenza Virus.

Ferrets immunised as described in the legend to FIG. 2 were inoculated intratracheally on day 52 with $10^6$ TCID$_{50}$ of virus. Body weight losses are expressed as percentage of body weight before infection (upper panel). Lung weights are expressed as percentage of body weight, as an indicator of lung consolidation (middle panel). Lungs were observed macroscopically and scored for lung area percentage displaying consolidated areas (bottom panel). Mean values are displayed; error bars indicate standard deviations. The horizontal grey bar indicates the detection limit of the assay.

FIG. 4

Examples of Histopathologic Findings in Lungs of Ferrets After Inoculation.

A) Inflammatory infiltrates and loss of epithelial cells in the bronchiolar walls and cellular debris in the bronchiolar lumen observed in the lungs of unprotected ferrets mock-vaccinated with PBS or adjuvant only (IMM) or vaccinated with the non-adjuvanted sHA$_3$+sNA$_4$. B) Proteinaceous fluid (edema) and infiltrate of inflammatory cells in the alveoli of lungs of ferrets mock-vaccinated with PBS or adjuvant only (IMM) or vaccinated with the non-adjuvanted sHA$_3$+sNA$_4$. C) Peribronchiolar infiltrate and cellular debris in bronchiole of ferret vaccinated with sHA+IMM. D) Inflammatory infiltrate in the alveolar septa and hypertrophy and hyperplasia of type II pneumocytes in lungs of ferrets vaccinated with sHA+IMM. E) Peribronchiolar infiltrate observed in lungs of ferrets of the sNA+IMM and sHA+sNA+IMM groups. F) Absence of inflammatory cells and hyperplasia of type II pneumocytes in alveoli of lungs of ferrets of the sNA+IMM and sHA+sNA+IMM groups. H&E staining; magnification 20× (bronchioli) and 40× (alveoli).

FIG. 5

Viral Titers in Lungs, Nose and Throat of Challenge-Inoculated Animals.

Virus replication in the ferrets immunised and challenged as described in the legend to FIG. 3 was analyzed 4 days after inoculation. Virus titers were determined in lung homogenates (upper panel), nose swaps (middle panel) and throat swaps (bottom panel). Titers were assayed by means of end-point titration in MDCK cells. Each dot represents the result of one ferret. Horizontal lines represent means. The horizontal grey bar indicates the detection limit of the assay.

FIG. 6

Induction of Cross-Neutralising Antibodies by Vaccination with Multimeric 2009 A(H1N1) Influenza Virus sHA3 and sNA4 Antigens.

(A) Sera of ferrets immunised twice with sHA$_3$ or sHA$_3$+sNA$_4$, both in adjuvant, as described in the legend to FIG. 2, were tested in an HI assay for activity towards different influenza viruses including Al/wine/shope/1/56, A/Italy/1443/76, A/NL/386/86, A/Iowa/15/30, A/NL/25/80, A/NewJersey/8/76, A/PR/8/34 and IVR/148 influenza H1N1. Mean titers are displayed; error bars indicate standard deviation. (B) Sera of ferrets immunised once or twice with sNA$_4$ or sHA$_3$+sNA$_4$, both in adjuvant, were pooled and tested in a NI assay for activity against the sNA$_4$ of A/Kentucky/UR06-0258/2007(H1N1) and A/turkey/Turkey/1/2005(H5N1) influenza virus. The NA of A/California/04/2009(H1N1) was taken along as a positive control. Positive control sera specific for A/NL/602/09(H1N1) or A/turkey/Turkey/1/2005(H5N1) influenza virus were obtained from a ferret infected with these viruses. Average titers of two replicates are displayed; error bars indicate standard deviations. The horizontal grey bar indicates the detection limit of the assay.

DETAILED DESCRIPTION

The invention regards a composition comprising at least one ISCOM complex and at least one ectodomain from at least one HA domain and at least one ectodomain from at least one NA domain from an influenza virus, wherein the extodomains represent ectodomains isolated from the influenza virus.

The ectodomain is the domain of a membrane protein that extends into the extracellular space. Ectodomains are usually the part of a protein that initiates contact with surface which leads to signal transduction. In the composition it may act as an antigen and the composition may be used as a vaccine.

Isolated means that the ectodomain is substantially isolated from other proteins and from the rest of the NA and HA proteins respectively of the influenza virus. Minor rest amino acids may be present. The ectodomain may be the full ectodomain or a part thereof having the same enzymatic and/or antigenic activity. According to one embodiment the part of the ectodomain may be the head domain thereof. Such ectodomains being the full ectodomain or a part thereof having the same enzymatic and/or antigenic activity may be isolated from influenza virus or synthetically produced. They may be presented separated from each other or linked together.

According one embodiment the ectodomain is a soluble ectodomain or a soluble head domain.

One or more of the ectodomains from at least one hemagglutinin domain and one or more of the ectodomains from at least one neuraminidase domain from the same or different influenza virus species or strains may be presented as hybridproteins, which may be recombinant.

Recombinantly produced HA and NA antigens allow the development of vaccines in which the relative amounts of both antigens can be easily controlled. Eukaryotic expression systems, both mammalian and insect, are the preferred platforms for production of such glycoproteins in view of their better preservation of the proteins' natural antigenic structure. Hybridproteins may be produced as described in Example 1 and according to Genscript (genscript.com).

The influenza virus may be chosen from sub serotypes of influenza e.g. from H×Ny, wherein x is 1-16 and y is 1-9. Thus x may be 1, 2, 3, 4, 5, 6, 7, 8, 9, 10, 11, 12, 13, 14, 15 and 16 and y may be 1, 2, 3, 4, 5, 6, 7, 8, 9. The influenza virus may be from any species such as humans, bird, cattle, e.g. bovine species, swines, sheep, goats. Bird influenza virus e.g. $H_{1-6} N_{1-9}$ or human influenza virus $H_{1-3} N_{1-2}$ or any combination of ectodomains from NA and HA thereof may be used. The NA ectodomains and/or the HA ectodomains may be from different species of influenza virus, e.g. of human and bird influenza virus. Thus, one or more human and bird NA ectodomains may be combined with one or more human and bird HA ectodomains, whereby the NA and HA may be of different types of HxNy.

According to one embodiment the influenza virus is an influenza A such as N1 H1 virus e.g. chosen from the 1918 $H_1N_1$ influenza virus (A/South Carolina/1/18) and/or the 2004 H5N1 (A/Vietnam/1203/04) H1N1 A/California/07/2009 virus and/or the A/California/04/2009 and/or the A/California/09/2009 and/or A/Kentucky/UR06-0258/2007 (H1N1) and/or A/turkey/Turkey/1/2005(H5N1).

One or more ectodomains (multimers) from NA and from HA may be used. The composition may comprise 1-5 ectodomains from at least one hemagglutinin domain and 1-5 head domains from at least one neuaminidase domain.

According to one embodiment the at least one hemagglutinin ectodomain is chosen from the trimeric HA extodomain (a.a. 17-522) of the A/California/09/2009.

According to one embodiment the least one neuraminidase head domain is chosen from the tetrameric NA head domain (a.a. 75-469) of the A/California/09/2009 virus. The sequence of the A/California/09/2009 protein is known in the art e.g. through ncbi.nlm.nih.gov (protein 227809830 and protein 227809834).

The ISCOM complexes may be used as adjuvants and immune modulating agents. They may be ISCOM and/or ISCOM matrix complexes.

The ISCOM-matrix complex and/or the ISCOM complex may be used together with one or more of antigens intended to elicit immune response to influenza infection. The antigens and ISCOM-matrix complex and/or ISCOM-complex may be administered in mixture or separately.

An ISCOM matrix complex comprises at least one glycoside and at least one lipid. The glycoside has adjuvant effect and is preferably a saponin especially form *Quillaja saponaria* Molina (Quil A). The lipid is at least a sterol such as cholesterol and optionally also a phospholipid. The ISCOM matrix complexes may also contain one or more other immunomodulatory (adjuvant-active) substances, not necessarily a glycoside, and may be produced as described in EP 0 436 620 B1.

An ISCOM complex contains at least one glycoside, at least one lipid, and at least one kind of antigen substance or epitope. These antigen substances may be of different kind such as proteins and peptides, glycoproteins and glycopeptides, carbohydrates etc. The glycoside has adjuvant effect and is preferably a saponin especially form *Quillaja saponaria* Molina (Quil A). These complexes enhance the immunogenicity of the included antigens and may also contain one or more immunomodulatory (adjuvant-active) substances. ISCOMs may be prepared as described in EP 0 109 942 B1, EP 0 242 380 B1 and EP 0 180 546 B1. Moreover, a transport and/or passenger antigen may be used, as described in EP 9600647-3 (PCT/SE97/00289).

The ectodomain antigens may be mixed with ISCOM matrix complex and/or ISCOM complex, associated or conjugated on to ISCOM matrix complex or mixed with ISCOM or be coupled onto ISCOM complexes. The prepared ISCOM complex may comprise one or more other antigens than the ectodomain antigens. According to one embodiment one or more ectodomain antigens may be used integrated into ISCOM complex. Such ISCOM complex may then be mixed with one or more ectodomain antigens. One or more antigens may be used and a transport and passenger antigen may be used as described in EP 9600647-3 (PCT/SE97/00289).

In order to be integrated into ISCOM particles the antigens need to have some hydrophobic portion or be electrostatic attached to an ISCOM Matrix. Antigens that do not have hydrophobic portions may be coupled to such molecules. Hydrophobic molecules and coupling methods are described in EP 180564.

The lipid comprised in the immunogenic complex is at least a sterol such as cholesterol and optionally also a phospholipid. The lipid(s) used are particularly those described in the applicant's patent EP 0 109 942 B1 in particular on p. 3 and in patent EP 0 436 620 B1 on p. 7 lines 7-24. Especially sterols such as cholesterol and phospholipids such as phosphatidylethanolamin and phosphatidylcolin are used.

Lipid-containing receptors that bind to the cell-binding components, such as glycolipids including the cholera toxin's receptor, which is the ganglioside GM1, and fucosed blood group antigen may be used. The cell-binding components can then function as mucus targeting molecule and be bound to the lipid-containing substances through simply mixing them with complexes that contain them. ISCOM complexes comprising receptors are described in e.g. WO 97/30728.

In one embodiment of the invention, the glycoside in the immunogenic complex for use in vaccination against influenza is a saponin fraction from *Quillaja saponaria* Molina.

Any sub fragments of *Quillaja saponaria* Molina saponins may also be used. Moreover, any combination of sub fragments of *Quillaja saponaria* Molina may be used. Thus, two or more sub fragments may each be integrated into an ISCOM complex or ISCOM-matrix complex.

The term "a saponin fraction from *Quillaja saponaria* Molina" is used throughout this specification and in the claims as a generic description of a semi-purified or defined saponin fraction of *Quillaja saponaria* or a substantially pure fraction. It is important that the fraction does not contain as much of any other fraction to negatively affect the good results that are obtained when the mixtures of ISCOM complexes or ISCOM matrix complexes comprising essentially one fraction is used.

According to one embodiment, there is provided an immunogenic complex for use according to the invention, further comprising, as part of the immunogenic complex or in mixture therewith, at least an additional adjuvant other than a saponin fraction from *Quillaja saponaria* Molina or at least one other glucoside or saponin than the one or the ones integrated into the ISCOM matrix or the ISCOM complex. Examples of useful non saponin adjuvants are different oils and $Al(OH)_3$ Examples of additional adjuvants that can be incorporated in the ISCOM complex and ISCOM matrix complex, respectively or mixed therewith, are any adjuvant, natural or synthetic, with desired immunomodulatory effect, e.g. naturally occurring, or derivatives thereof, synthetic or semi synthetic saponin molecules derived from crude saponin extract of *Quillaja saponaria* Molina; e.g. saponins and saponin fractions from Quil A, cell wall skeleton, block polymers, e.g. hydrophilic block copolymers, e.g. CRL-1005, TDM (threhalose di mucolate), lipopeptides, LPS and LPS-derivatives, Lipid A from various bacterial species and derivatives thereof, (e.g., monophosphoryl lipid A, muramyl di or tri peptide or muramyl dipeptide), MDP-derivatives, (e.g. fatty acid derivatives), substituted MDP, threonyl analogues of MDP (and derivatives thereof), CpG variants, CpGODN variants, endogenous human and animal immunomodulators, (e.g. GM-CSF). IL-2, adjuvant active bacterial toxins, native or modified toxins, (e.g. cholera toxin CT, and its subcomponents CTB and CTA1), thermo labile toxin (LT) of *E. coli, Bordetella pertussis* (BP) toxin and the filamentus heamagglutenin of BP. DDA, poly anions such as Dextran sulphate and lipopolysaccharides such as saponins (other than Quil A), see ("Future prospects for vaccine adjuvants", Warren, H. S. (1988) CRC Crit. Rev. Immunol. 8:2, 83-101; "Characterisation of a non-toxic monophosphoryl lipid A", (1987) Johnson, A. G. et al, Rev. Infect. Dis. 9:5, 5512-5516; "Developmental status of synthetic immunomodulators", Berendt, M. J. et al (1985), Year Immunol. 193-201; "Immunopotentiating conjugates", Stewart-Tull, D. E., Vaccine, 85, 3:1, 40-44) all of which are incorporated by reference.

The ISCOM particle may be an ISCOM complex or an ISCOM matrix complex made from any saponin. The adjuvant fraction A and the other at least one adjuvant may also be coupled on to the different or the same ISCOM particles or ISCOM matrix particles or one or more of the adjuvants may be mixed with the ISCOM particles.

In order to be integrated into ISCOM particles the adjuvants need to have some hydrophobic molecule. Adjuvants that do not have hydrophobic portions may be coupled to such molecules. Hydrophobic molecules and coupling methods are described in EP 180564. Preferably the adjuvants are integrated into different ISCOM particles.

In another embodiment of the invention the adjuvant fraction A of Quil A is integrated into ISCOM particles, whereas the other at least one adjuvant are not integrated into ISCOM particles and are used in free form in the composition.

In another preferred embodiment of the invention the adjuvant fractions of Quil A is integrated into ISCOM particles or ISCOM matrix particles, whereas other adjuvants are not integrated into ISCOM particles or ISCOM matrix particles and are used in free form in the composition.

In another especially preferred embodiment the composition comprises fraction A of Quil A integrated into ISCOM particles or ISCOM matrix particles and at least one other adjuvant, which is not integrated into ISCOM particles or ISCOM matrix particles.

In another preferred embodiment the at least other adjuvant is MPL or cholera toxin CT. The MPL or cholera toxin may be integrated into the same ISCOM particle or ISCOM matrix particle or into each a different ISCOM particle or ISCOM matrix particle. Preferably the MPL or cholera toxins are in free form.

The saponin fraction from *Quillaja saponaria* Molina for use in the ISCOM matrix complex, the ISCOM complex and/or the at least one additional adjuvant may be selected from fraction A, fraction B, fraction C of *Quillaja saponaria* Molina, a crude fraction of *Quillaja saponaria* Molina, QA 1-21. However, with modern powerful separation techniques more than 60 different structures are reported and described (Bankefors et al., J Chrom B Analyt Technol Biomed Life Sci in press; Bankefors et al., Rapid Commun Mass Spectrom 22:3851; Broberg et al., J Mass Spectrom 39:691; Nyberg et al., Anal Chem 75:268; Guo and Kenne Phytochemistry 55:419; Nord and Kene Carbohydr Res 329:817; Guo and Kenne Phytochemistry 54:615; Guo et al., Phytochemistry 53: 861; Nyberg et al., Carbohyd. Res 323:87: Nord and Kenne Carbohyd. Res 320:70 Guo et al., Phytochemistry 48:175).

When prepared as described herein, Fractions A, B and C of *Quillaja saponaria* Molina each represent groups or families of chemically closely related molecules with definable properties. The chromatographic conditions under which they are obtained are such that the batch-to-batch reproducibility in terms of elution profile and biological activity is highly consistent.

The term "one saponin fraction from *Quillaja saponaria* Molina." is used throughout this specification and in the claims as a generic description of a semi-purified or defined saponin fraction of *Quillaja saponaria* or a substantially pure fraction. It is important that the fraction does not contain as much of any other fraction to negatively affect the good results that are obtained when the mixtures of ISCOM or ISCOM matrix comprising essentially one fraction is used. The saponin preparation may, if desired, include minor amounts for example up to 40% by weight, such as up to 30% by weight, up to 25% by weight, up to 20% by weight, up to 15% by weight, up to 10% by weight, up to 7% by weight, up to 5% by weight, up to 2% by weight, up to 1% by weight, up to 0.5% by weight up to 0.1% by weight of other compounds such as other saponins or other adjuvant materials.

The saponin fractions A, B and C according to the present invention are as described in WO 96/11711, the B3, B4 and B4b fractions as described in EP 0 436 620; the fractions QA1-21 are as described in EP 0 3632 279 B2. The fractions QA-1-2-3-4-5-6-7-8-9-10-11-12-13-14-15-16-17-18-19-20 and 21 of EP 0 3632 279 B2, especially QA-7, 17-18 and may be used. They are obtained as described in EP 0 362 279 B2, especially on page 6 and in Example 1 on page 8 and 9.

Any type of crude or semi-purified fractions of saponins from *Quillaja saponaria* Molina may be used. A crude fraction of *Quillaja saponaria* Molina used for the purpose of this patent is any saponin composition somewhat purified from other lipophilic non-saponin components. This may be any saponin fraction which is a purified but non fractionated preparation of *Quillaja saponaria* Molina Such crude fraction wherein the saponins are not separated from each other may be produced and delivered from e.g., Desert King Chile (desertkingchile.cl), Sigma-Aldrich (sigmaaldrich.com), Berghausen (berghausen.com), Brenntag Biosector (brenntag-biosector.com).

Fractions A, B and C described in WO 96/11711 are prepared from the lipophilic fraction obtained on chromatographic separation of the crude aqueous *Quillaja saponaria* Molina extract and elution with 70% acetonitrile in water to isolate the lipophilic fraction. This lipophilic fraction is then separated by semi preparative HPLC with elution using a gradient of from 25% to 60% acetonitrile in acidic water. The fraction referred to herein as "Fraction A" or "QH-A" is, or corresponds to, the fraction, which is eluted at approximately 39% acetonitrile. The fraction referred to herein as "Fraction B" or "QH-B" is, or corresponds to, the fraction, which is eluted at approximately 47% acetonitrile. The fraction referred to herein as "Fraction C" or "QH-C" is, or corresponds to, the fraction, which is eluated at approximately 49% acetonitrile.

According to one embodiment a crude fraction of saponins is used.

According to another embodiment a crude fraction of saponins may be used together with any other purified saponin fraction, e.g. the different saponin fractions mentioned above.

According to one embodiment of the invention the saponin fraction from *Quillaja saponaria* Molina, which is integrated into an ISCOM matrix complex or an ISCOM complex, or the at least one additional adjuvant, which also is integrated into the ISCOM or ISCOM matrix complex or mixed therewith, is selected from fraction A, fraction B, fraction C of *Quillaja saponaria* Molina, a semipurified preparation of *Quillaja saponaria* Molina, a purified preparation of *Quillaja saponaria* Molina, or any purified subfraction e.g., QA 1-21.

ISCOM matrix and/or ISCOM complexes, comprising respectively at least two saponin fraction *Quillaja saponaria* may be used. Any combinations of weight % of different saponin fractions may be used. Any combination of weight % of any two fractions may be used e.g. any weight % of fraction A and any weight % of another fraction, e.g. any crude saponin fraction or fraction C of Quillaja *saponaria* Molina respectively. The ISCOM matrix and/or ISCOM complexes may comprise from, 0.1 to 99.9 by weight, 5 to 95% by weight, 10 to 90% by weight 15 to 85% by weight, 20 to 80% by weight, 25 to 75% by weight, 30 to 70% by weight, 35 to 65% by weight, 40 to 60% by weight, 45 to 55% by weight, 40 to 60%, by weight, 50 to 50% by weight, 55 to 45% by weight, 60 to 40% by weight, 65 to 35% by weight, 70 to 30% by weight, 75 to 25% by weight, 80 to 20% by weight, 85 to 15% by weight, 90 to 10% by weight, 95 to 05% by weight, 50 to 99% by weight, 60 to 90% by weight, 70 to 90% by weight, 75 to 85% by weight, of one saponin fraction, e.g. fraction A of *Quillaja saponaria* Molina and the rest up to 100% in each case of interval of another saponin e.g. any crude fraction or any other faction e.g. fraction C of *Quillaja saponaria* Molina, counted on the sum of the weights of the saponin fractions, of *Quillaja saponaria* Molina in the ISCOM matrix and/or ISCOM complexes.

According to one embodiment, there is provided an ISCOM matrix and/or ISCOM complex for use according to the invention, comprising from 5-99% by weight of one fraction, e.g. fraction A of *Quillaja saponaria* Molina and the rest up to 100% of weight of another fraction e.g. a crude saponin fraction or fraction C of *Quillaja saponaria* Molina counted on the weight of fraction A and fraction C.

According to another embodiment, there is provided an ISCOM matrix and/or ISCOM complex for use according to the invention, comprising from 40% to 99% by weight of one fraction, e.g. fraction A of *Quillaja saponaria* Molina and from 1% to 60% by weight of another fraction, e.g. a crude saponin fraction or fraction C of *Quillaja saponaria* Molina counted on the weight of fraction A and fraction C.

According to yet an embodiment, there is provided an ISCOM matrix and/or ISCOM complex for use according to the invention, comprising from 70% to 95% by weight of one fraction e.g. fraction A of *Quillaja saponaria* Molina and from 30% to 5% by weight of another fraction, e.g. a crude saponin fraction or fraction C of *Quillaja saponaria* Molina counted on the weight of fraction A and fraction C.

In one embodiment, there is provided an ISCOM matrix and/or ISCOM complex for use according to the invention, wherein the saponin fraction from *Quillaja saponaria* Molina is selected from any one of QA 1-21.

According to one aspect of the invention, there is provided a composition e.g. a vaccine comprising at least one ISCOM matrix and/or ISCOM complex according to the invention together with one or more ectodomain antigens and one or more pharmaceutically acceptable, excipients carriers and/or diluents and/or further adjuvants, for use in vaccination against influenza.

Such a composition may comprise one or more different types of ISCOM-matrix complexes particles and/or one or more different types of ISCOM complexes particles, each individual type complex particles comprising one saponin fraction from *Quillaja saponaria* Molina, wherein the saponin fraction in one complex is different from the saponin fraction in the other complex particles. The composition may comprise several particles. However, according to one embodiment one particle may only comprise one single type of fraction of *Quillaja saponaria* Molina, Thus, one type of substantially pure saponin fraction or a crude saponin fraction may be integrated into one ISCOM matrix complex or particle and another type of substantially pure saponin fraction or a crude saponin fraction may be integrated into another ISCOM matrix complex or particle. A composition or vaccine may comprise at least two types complexes or particles each type having one type of saponins integrated into physically different particles.

In the compositions, mixtures of ISCOM matrix complex particles and/or ISCOM complex particles may be used in which one saponin fraction *Quillaja saponaria* Molina and another saponin fraction *Quillaja saponaria* Molina are separately incorporated into different ISCOM matrix complex particles and/or ISCOM complex particles. Any combinations of weight % of the different ISCOM complexes based on their content of one saponin fraction and any other saponin fraction may be use, e.g. fraction A and another fraction, e.g. any crude saponin fraction or fraction C of *Quillaja saponaria* Molina respectively may be used. These % figures may be the same as mentioned above regarding possible mixtures of saponin fractions in one and the same ISCOM matrix complex particle and/or ISCOM complex particle, now however in separate ISCOM matrix complex particles and/or ISCOM complex particles In still another embodiment the Quil A fraction A is incorporated into an ISCOM particle or ISCOM matrix particle and the at least one other adjuvant is incorporated into each a different ISCOM particle or ISCOM matrix particle, or one or more other fractions of Quil A or one or more other adjuvants are incorporated into the same ISCOM or ISCOM matrix particle but different form the particle into which the Quil A fraction A was incorporated or the other at least one adjuvant is/are in free form.

In the composition, fraction A may be combined with at least one of fractions C and crude saponin fraction of from *Quillaja saponaria* Molina e.g. fraction Q, in the same or different ISCOM complexes and/or ISCOM-matrix complexes.

By combining ISCOM-matrix complexes comprising different fractions of *Quillaja saponaria* Molina it is possible to produce compositions that are less toxic to the animals. Hence, in one embodiment, the composition for use according to the invention comprises fraction A in combination with at least one of fractions C and Q, in the same or different ISCOM complexes and/or ISCOM-matrix complexes.

The composition may further comprise one or more pharmaceutically acceptable excipients, carriers and/or diluents and further adjuvants The composition may comprise at least one other adjuvant than a saponin integrated into an ISCOM complex particle or an ISCOM matrix particle. This further adjuvant may be a saponin fraction from *Quillaja saponaria* Molina, which may be bound on to or mixed with the immunogenic ISCOM matrix complex particle or ISCOM complex particle. It may also be another type of saponin or any other type of adjuvant which may be integrated into, bound on to or mixed with the immunogenic ISCOM matrix complex particle or ISCOM complex particle.

The composition may be a vaccine.

The term "vaccine" herein refers to a material capable of producing an immune response. A vaccine according to this invention would produce immunity against influenza.

The compositions may be used prophylactic to prevent infection from occurring or may be therapeutic to treat pre-existing infections, or may be for the production of immunological reagents.

Other antigens than antigens from ectodomains from influenza virus may be integrated into the ISCOM complex, coupled on to ISCOM complex or onto ISCOM matrix complex or mixed with ISCOM complex or ISCOM matrix complex. The invention also regards combination vaccines or combination veterinary medicines for treatment.

The formulation of compositions according to the invention is well known to persons skilled in the art. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and is described, by way of example, in Remington's Pharmaceutical Sciences, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

According to one other aspect the composition may be used as an immune stimulating medicine, immune modulating pharmaceutical or a vaccine e.g. against influenza for vertebrates, e.g. birds and mammals. The mammal may be a human, companion animals such as cats, dogs, horses, birds such as parrots, economical important species such as cattle, e.g. bovine species, swines, sheep, goats or ferrets, minks.

The invention also regards a kit comprising at least two compartments, wherein one compartment comprises a composition comprising at least one ISCOM complex and at least one ectodomain from at least one hemagglutinin domain and at least one ectodomain from at least one neuraminidase domain from one or more influenza virus and the other compartment comprises instructions for use.

According to another aspect the invention relates to a kit comprising at least two compartments, wherein one compartment comprises ISCOM complex and/or ISCOM matrix complex and the other compartment comprises at least one ectodomain from at least one hemagglutinin domain and at least one ectodomain from at least one neuraminidase domain.

Applicants have especially addressed the efficacy of recombinantly produced HA and NA subunits of the 2009 A(H1N1) influenza virus as vaccines against homotypic influenza virus in a ferret model, with particular emphasis on the contribution of the NA antigen. Soluble, multimeric forms of the HA and NA antigens of the pandemic H1N1 virus have been expressed in a mammalian expression system. The glycoproteins were purified by single-step affinity chromatography and subsequently ferrets were immunised either with one or with both antigens and with or without ISCOM Matrix M as an adjuvant. The animals responded serologically to both antigens, but only when administered with the adjuvant. Interestingly, inclusion of NA in the vaccine enhanced the levels of HA antibodies and of virus neutralising activity. Significant protection, as judged particularly from the dramatically (5 $\log_{10}$ units) reduced viral lung titers, was observed upon homologous challenge in the animals immunised with HA-containing vaccines in combination with ISCOM Matrix M. Interestingly, ISCOM matrix M adjuvanted formulations containing NA clearly reduced the clinical effects of infection.

All publications mentioned herein are incorporated herein as reference, to the greatest extent permitted by law.

The invention will now be further described by the following non-limiting examples.

EXAMPLES

Example 1 Preparation of HA and NA Antigens

Materials and Methods
Influenza a Challenge Virus

Influenza virus A/Netherlands/602/2009 was isolated from the first case of a laboratory confirmed 2009 A(H1N1) infection in The Netherlands by inoculation of 11-day old embryonated chicken eggs [15]. Virus stocks of influenza virus A/Netherlands/602/2009(H1N1) were prepared by infecting confluent Madin-Darby Canine Kidney (MCCK) cells. After cytopathologic changes were complete, culture supernatants were cleared by low speed centrifugation and stored at −70° C. Infectious virus titers were determined in MCCK cells as described previously [16]. All experiments with these viruses were performed under Bio Safety Level (BSL)-3 conditions.

Preparation of HA and NA Antigens

Human codon optimized sequences encoding the soluble hemagglutinin ectodomain (sHA; a.a. 17-522) and the neuraminidase head domain (sNA; a.a. 75-469) of influenza virus A/California/04/2009(H1N1) were synthesised (GenScript) and cloned into a derivative of expression plasmid pS1-Ig [17] for expression in HEK293T cells. The HA gene was preceded by a sequence encoding an N-terminal CD5 signal peptide and followed by sequences encoding a C-terminal artificial GCN4 trimerisation domain (GCN4-pII) [18] and a Strep-tag for affinity purification (IBA GmbH) as described recently [19, 20]. The NA gene was preceded by sequences successively coding for an N-terminal CD5 signal peptide, a double Strep-tag (OneSTrEP; IBA GmbH) and an artificial GCN4 tetramerisation domain (GCN4-pLI) [18].

Production of $sHA_3$ and $sNA_4$ Antigens

Figure 1:
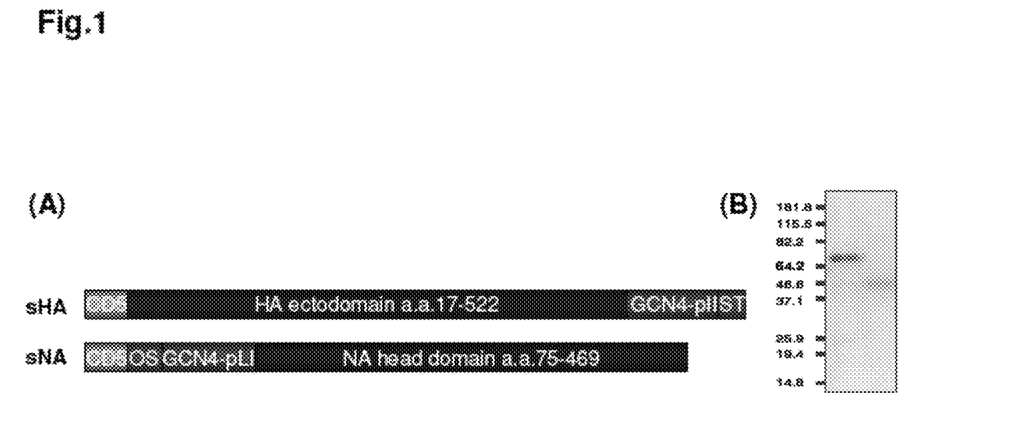

Constructs were designed to express the trimeric HA ectodomain (a.a. 17-522) and the tetrameric NA head domain (a.a. 75-469) of the 2009 A(H1N1) influenza virus as pictured in FIG. 1A. The $sHA_3$ and $sNA_4$ proteins were produced by expression in HEK293T cells and purified from the culture medium by affinity chromatography yielding glycoproteins of the expected size (FIG. 1B). Gel filtration analysis indicated the trimeric and tetrameric oligomeric nature of the HA and NA subunits, respectively (data not shown). The multimeric complexes were also biologically active, further confirming their native state, as judged by their sialic acid binding ($sHA_3$; manuscript in preparation) and neuraminidase activity ($sNA_4$; below).

Example 2 Protein Expression and Purification

HEK293T cells were transfected with the sHA and sNA expression plasmids using polyethyleneimine (PEI) in a 1:5 ratio (μg DNA:μg PEI). After a 6 h incubation period the transfection medium was replaced by 293 SFM II expression medium (Invitrogen) supplemented with sodium bicarbonate (3.7 g/liter), glucose (2.0 g/liter), Primatone RL-UF (3.0 g/liter), penicillin (100 units/ml), streptomycin (100 uq/ml), glutaMAX (Gibco), and 1.5% DMSO. Tissue culture supernatants were harvested 5-6 days post transfection and sHA and sNA proteins were purified from the culture medium using Strep-Tactin affinity chromatography (IBA GmbH). sHA and sNA protein expression and purification was confirmed by western blotting using a Strep-Tractin-HRP conjugate (IBA GmbH; data not shown) and SDS-PAGE analysis. Oligomerization of the proteins was determined by gel filtration chromatography and by blue-native-PAGE analysis. Quantification of protein amounts was done using BSA as a reference.

Example 3 Immunisations and Infections

Ferrets

Healthy young adult outbred female ferrets (*Mustela putorius furo*; between 6 and 12 months old) were purchased from a commercial breeder. The animals were checked for the absence of antibodies against circulating seasonal A/H1N1 and A/H3N2 influenza viruses and against the swine-origin influenza A/NL/602/09 virus by hemagglutination inhibition assay. An independent animal ethics committee approved the experimental protocol before the start of the experiment.

The ISCOM matrix M adjuvant was prepared as described in WO2004/004762. 75 micrograms of a composition comprising 85% Matrix A and 15% Matrix C in PBS was added to the antigens.

Immunisations and Infections

Thirty-six seronegative ferrets were divided into six groups of 6 ferrets each and vaccinated twice with the following formulations: 3.75 µg $sHA_3$+3.75 µg $sNA_4$ in phosphate buffered saline (PBS) (group 1); 3.75 µg $sHA_3$ in ISCOM Matrix M (IMM, Isconova, Uppsala, Sweden) (group 2); 3.75 µg $sNA_4$ in IMM (group 3); 3.75 µg $sHA_3$+3.75 µg $sNA_4$ in IMM (group 4); PBS (group 5); IMM (group 6). Vaccinations were performed with an interval of 20 days under anesthesia with ketamine in the quadriceps muscles of the hindleg in a total volume of 1 ml. Ferrets were housed in groups and received food and water ad libitum. At 32 days after the last vaccination, the animals were anesthetised with ketamine/medetomidine (reversed with atipamezole), weighed and subsequently challenged intratracheally with $1\times10^6$ $TCID_{50}$ of influenza A/NL/602/09(H1N1) in a volume of 3 ml PBS [21, 22]. Ferrets were subsequently monitored three times daily for the development of clinical signs. Before infection and two and four days after infection, nose and throat swabs of each ferret were collected while ferrets were anesthetised with ketamine. Four days after inoculation, animals were weighed and subsequently euthanized by exsanguination while under anesthesia with ketamine and medetomidine. Necropsies were performed according to standard procedures. One ferret of group 1 died between the first and second vaccination due to reasons unrelated to the experiment.

Serology

Serum samples were collected before vaccination, at the day of second vaccination (day 20) and at the day of challenge (day 52). Sera were stored at −20° C. until use. Sera were tested for the presence of anti-HA antibodies using a hemagglutination inhibition assay (HI-assay) with 1% turkey erythrocytes and for the presence of virus neutralising antibodies using a micro virus neutralisation assay (VN-assay) as described previously [23, 24]. Sera were tested for the presence of antibodies reactive with influenza A/NL/602/09(H1N1). For this purpose, reverse genetics viruses were produced. The titers obtained with these viruses were comparable to those against the wild-type strains (data not shown). Positive control serum specific for influenza A/NL/602/09(H1N1) was obtained from a ferret infected with this virus [15]. Other H1N1 influenza viruses used in the HI-assay were A/Netherlands/386/86 (NL/86), A/Netherlands/25/80 (NL/80), A/New Jersey/8/76 (NJ/76), A/Swine/shope/1/56 (Sw/56), A/Italy/1443/76 (It/76), A/Iowa/15/30 (10/30), A/Puerto Rico/8/34 (Pr/34) and A/Brisbane/59/07 (IVR-148 vaccine strain; IVR/148). Serum samples of ferrets infected with these viruses were used as a positive control in this assay [25].

Sera were also tested for the presence of neuraminidase inhibiting (NI) antibodies using a previously described fetuin-based assay [26]. Briefly, 96-well Nunc MaxiSorp plates were coated overnight at 4° C. with 100 µl of 5 µg/ml fetuin. Sixty-µl volumes of serially diluted serum samples were incubated for 30 minutes at 37° C. with an equal volume of $sNA_4$ containing culture supernatant (prediluted in PBS-Ca/Mg [0.901 mM/0.493 mM] to give a half-maximum $OD_{450}$ of 1.5) after which 100 µl of the mixture was added to the fetuin-coated wells. After one hour incubation at 37° C., the plates were washed and neuraminidase activity was subsequently measured by adding peroxidase-labelled peanut agglutinin (2.5 µg/ml; Sigma), incubating for 1 h at room temperature, washing the plates and adding 100 µl of peroxidase substrate (TMB) to each well. After 5 minutes, the reaction was stopped by the addition of 100 µl of 0.3 M phosphoric acid and OD values were measured at 450 nm using an ELISA reader (EL-808 [BioTEK]). To test the sera for cross-reactive NI antibodies, $sNA_4$ expression constructs similar to the ones described above for A/California/04/2009(H1N1) were also made for the head domains of A/Kentucky/UR06-0258/2007(H1N1) (a.a. 75-470) and A/turkey/Turkey/1/2005(H5N1) influenza virus (a.a. 55-449). Sera specific for influenza A/NL/602/09(H1N1) and A/turkey/Turkey/1/2005(H5N1) obtained from a ferret infected with these viruses were used as a positive control.

Virus Replication in the Upper and Lower Respiratory Tract

Samples of all lobes of the right lung and of the accessory lobe were collected of the infected ferrets, snap frozen on dry ice with ethanol and stored at −70° C. until further processing. Lung samples were weighed and subsequently homogenised with a FastPrep-24 (MP Biomedicals, Eindhoven, The Netherlands) in Hank's balanced salt solution containing 0.5% lactalbumin, 10% glycerol, 200 U/ml penicillin, 200 µg/ml streptomycin, 100 U/ml polymyxin B sulfate, 250 µg/ml gentamycin, and 50 U/ml nystatin (ICN Pharmaceuticals, Zoetermeer, The Netherlands) and centrifuged briefly. Nose and throat swabs were stored directly at −70° C. in the same medium as used to homogenise the lung samples. Quadruplicate 10-fold serial dilutions of throat, nose and lung samples were used to infect MDCK cells as described previously [16]. HA activity of the culture supernatants collected 5 days post inoculation was used as indicator of infection. The titers were calculated according to the Spearman-Karber method and expressed as log $TCID_{50}$ per gram for lung tissue or per ml for swabs [27].

Histopathology

Four days post inoculation (dpi) with influenza A/NL/602/09 virus, ferrets were euthanized and lungs were observed macroscopically and weighed before samples from the right lungs were collected to determine the virus titers. Subsequently left lung lobes were inflated with 10% neutral buffered formalin. After fixation and embedding in paraffin, lungs were sectioned at 4 µm and tissue sections were examined by staining with hematoxylin and eosin (HE).

Statistical Analysis

Significance among animal groups was analysed by one-way ANOVA and Tukey test subsequent to ANOVA. Differences were considered significant at P<0.05.

Results

Antibody Responses Induced by Immunisation with sHA3 and sNA4

The glycoproteins were tested for their ability to induce protective immunity against homologous virus challenge. Ferrets were immunised at days 0 and 20 with $sHA_3+sNA_4$ without adjuvant (sHA+sNA), with $sHA_3+sNA_4$ adjuvanted with ISCOM Matrix M (IMM; sHA+sNA+IMM), or with similarly adjuvanted $sHA_3$ (sHA+IMM) or $sNA_4$ (sNA+IMM). Sera were collected at the day of the second immunisation and pre-challenge (days 20 and 52) and antibody responses were measured by HI and VN assays against the homologous virus and by NI assay (FIG. 2). No responses with any of these assays were observed in control animals vaccinated with PBS or with adjuvant only, but also not in the animals immunised with the non-adjuvanted mixture of $sHA_3$ and $sNA_4$. In contrast, the immunisations with adjuvanted $sHA_3$ (sHA+IMM) induced high HI titers, with a geometric mean titer of 91 at day of challenge. Interestingly, the additional inclusion of $sNA_4$ (sHA+sNA+IMM) significantly increased the average HI titers to 468 ($p<0.05$; one-way ANOVA and Tukey test). Also the NI titrations revealed the adjuvant-dependent induction of NA antibodies, which were low after one (FIG. 2) but strongly boosted after two immunisations (FIG. 2). However, in this case no clear augmentation of these titers was observed due to the coadministration of $sHA_3$. Consistent with the observed HI titers, high VN titers were found both in the sHA-IMM and in the sHA+sNA+IMM vaccinated animals (FIG. 2). Also here the co-administration of the $sNA_4$ antigen with the sHA+sNA+IMM vaccine had resulted in an increase in the mean VN titer, average values ranging from 1:202 to 1:468 in the sHA+IMM and sHA+sNA+IMM groups, respectively.

Protection Against Clinical Signs after Infection with 2009 A(Ht Nt) Influenza Virus Vaccinated ferrets were challenged with $10^6$ $TCID_{50}$ 2009 A(H1N1) 5 weeks after the second vaccination. From day two after inoculation onwards, clinical signs were observed in inoculated ferrets which included breathing difficulties, lethargy, decreased appetite and weight loss. In general, only mild clinical signs were observed in ferrets of groups 2, 3 and 4, while more severe symptoms were observed in ferrets of groups 1, 5 and 6. Loss of body weight became obvious in the PBS- and IMM-vaccinated control groups as well as in the non-adjuvanted sHA+sNA vaccine group (FIG. 3). Interestingly, the animals immunised with sHA-IMM showed nearly similar weight losses, while body weights were not significantly affected after vaccination with both the $sNA_4$ containing formulations (groups sNA-IMM and sHA+sNA-IMM). More or less consistently, the lung weights of the ferrets determined post mortem showed a corresponding tendency of adjuvanted $sNA_4$-vaccinated animals having the least disease-related increase due to lung consolidation (FIG. 3).

Gross Pathologic and Histopathologic Findings in the Lungs of Ferrets

Four days after inoculation with influenza virus 2009 A(H1N1) virus, the lungs of the ferrets were examined macroscopically and weighed before samples were taken for assessing virus replication and histopathological changes. Dark red and firm consolidated areas were observed macroscopically in lungs of inoculated ferrets. The percentage of affected lung tissue was estimated and varied between groups. Mean percentages of affected areas in the lungs of about 50% were observed in ferrets of groups 1, 5 and 6, while the extent of consolidation was less pronounced in ferrets of groups 2, 3 and 4, which showed less than 25% of the lung area being affected (FIG. 3). Also the relative lung weight was lower in these groups compared to that in ferrets of groups 1, 5 and 6 (FIG. 3).

Histopathological changes observed at day 4 post inoculation in the lungs of ferrets mock-vaccinated with PBS or adjuvant only (IMM) or vaccinated with the nonadjuvanted $sHA_3+sNA_4$ were characteristic for a moderate to severe necrotizing broncho-interstitial pneumonia. Multifocally, many neutrophils and macrophages and variable numbers of erythrocytes, edema fluid and fibrin were present in the alveoli of the lungs of these ferrets. In addition, inflammatory infiltrates were present in the alveolar septa, in the bronchioles, in the bronchi and in the walls of bronchi and bronchioli. A dramatic reduction in histopathological changes was observed in the adjuvanted $sNA_4$-vaccinated animals (sNA+IMM and sHA+sNA+IMM groups), while ferrets immunised with sHA+IMM were partially protected from developing pathology (FIG. 4).

Protection Against Virus Replication in the Upper and Lower Respiratory Tract

To measure the effect of vaccination on the virus replication in the respiratory tract, virus titers were determined in lungs, throat and nose 4 days after inoculation. As shown in FIG. 5 the challenge virus replicated efficiently in the lungs of the control ferrets (PBS and IMM groups) and in the animals immunised with the non-adjuvanted mixture of $sHA_3$ and $sNA_4$ (sHA+sNA group), with mean viral titers of approximately $10^7$-$10^8$ $TCID_{50}$/gram tissue. These viral loads were reduced by about 5 $log_{10}$ units in the animals immunised with the $sHA_3$ protein in adjuvant (sHA+IMM group) and in animals co-immunised with $sHA_3$ and $sNA_4$ in adjuvant (sHA+sNA+IMM group). Mean viral loads were reduced by 2-3 $log_{10}$ units in animals immunised with adjuvanted $sNA_4$ antigen (sNA+IMM group).

High viral loads in the nose were observed in the control animals (PBS and IMM groups; FIG. 5) at day 4 after the challenge. Though not statistically significant due to the large variations in titers within groups, these viral loads appeared somewhat lower in the animals immunised with adjuvanted $sHA_3$ or adjuvanted $sNA_4$ or with the non-adjuvanted $sHA_3+sNA_4$ combination. The highest reduction of nose viral titers was found in animals immunised with the adjuvanted combination of $sHA_3$ and $sNA_4$ antigens. Viral titers in the throat were generally high and not significantly affected by vaccination except in the animals vaccinated with the adjuvanted combination of $sHA_3$ and $sNA_4$. These ferrets did not have detectable titers in the throat.

Cross-Reacting Antibody Responses Induced by Immunisation with $sHA_3$ and $sNA_4$ To investigate whether the antibodies induced by the $sHA_3$ and sNA4 antigens could cross-react with other $H1N_1$ influenza viruses we performed additional HI and NI assays with the post vaccination sera. As expected, the highest HI titers were measured against the homologous virus while various extents of cross-reactivity were observed with a range of other H1-strains (FIG. 6A). Thus, no cross-reactivity was detected for A/Swine/shope/1/56, A/Italy/1443/76, A/Iowa/15/30, A/PR/8/34 and IVR/148, whereas significant cross-reactivity was measured against A/NL/25/80 and A/NewJersey/8/76 and, particularly, against A/NL/386/86, more or less consistent with the sequence similarities of their antigenic domains (see table 1).

TABLE 1

Sequence homology of the antigenic regions within HA of different H1N1 strains.

| H1N1 strains: | GenBank Protein Accession number: | % sequence homology HA antigenic domains [30] relative to A/California/04/09 |
|---|---|---|
| A/California/04/09 | ACQ76318.1 | 100 |
| A/Netherlands/602/09 | ACQ45338.1 | 98.6 |
| A/Swine/shope/1/56 | * | n.a. |
| A/Italy/1443/76 | * | n.a. |
| A/Netherlands/386/86 | AAK51350.1 | 66.2 |
| A/Iowa/15/30 | AAD25303.1 | 76.1 |
| A/Netherlands/25/80 | AAK51352.1 | 67.6 |
| A/NewJersey/8/76 | AAA43210.1 | 78.9 |
| A/PuertoRico/8/34 | ACV89502.1 | 64.8 |
| A/Brisbane/59/07 (IVR-148 vaccine strain) | ADI99532.1 | 56.3 |

* sequence not available;
n.a. not applicable

Figure 2:
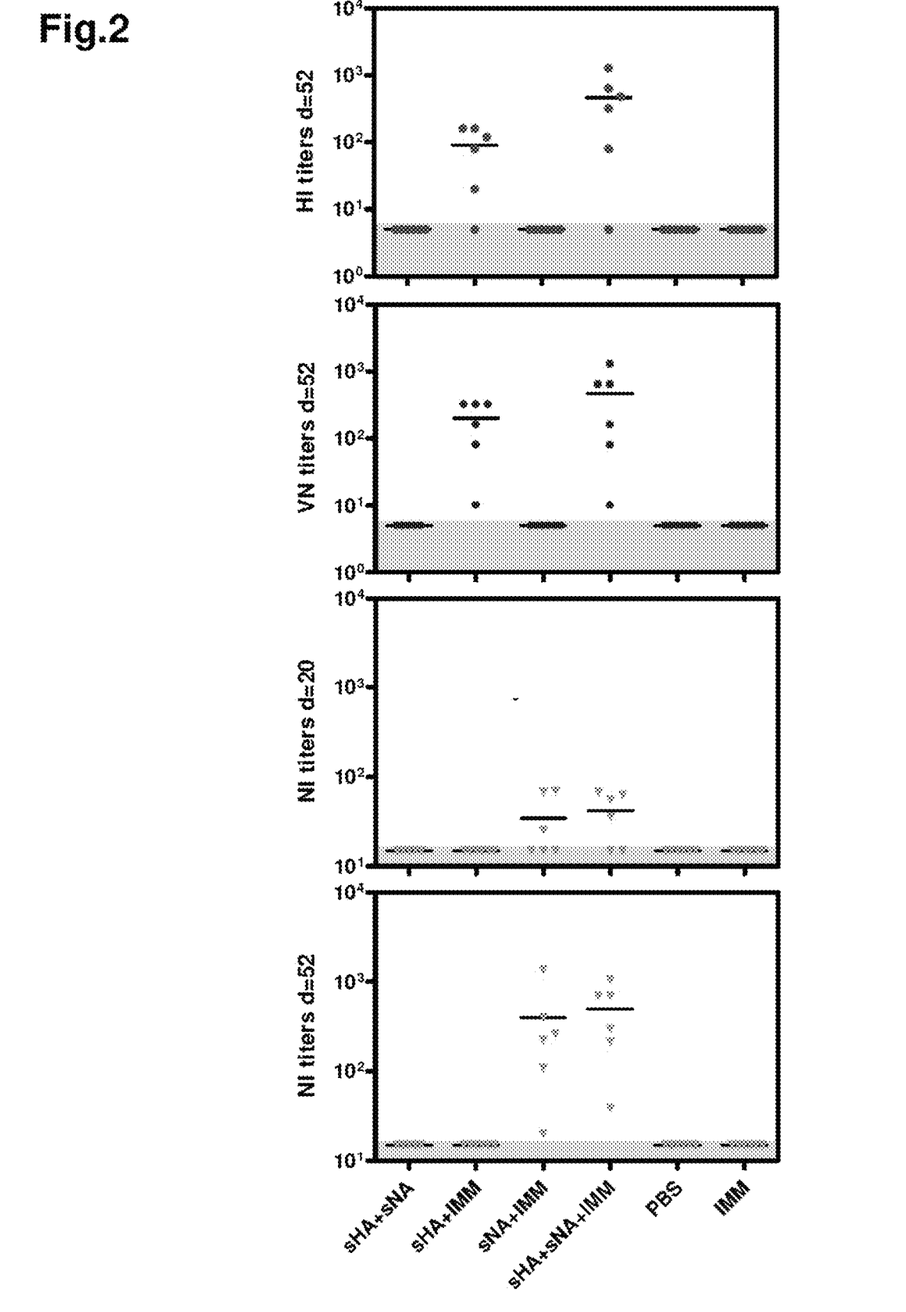
Figure 3:
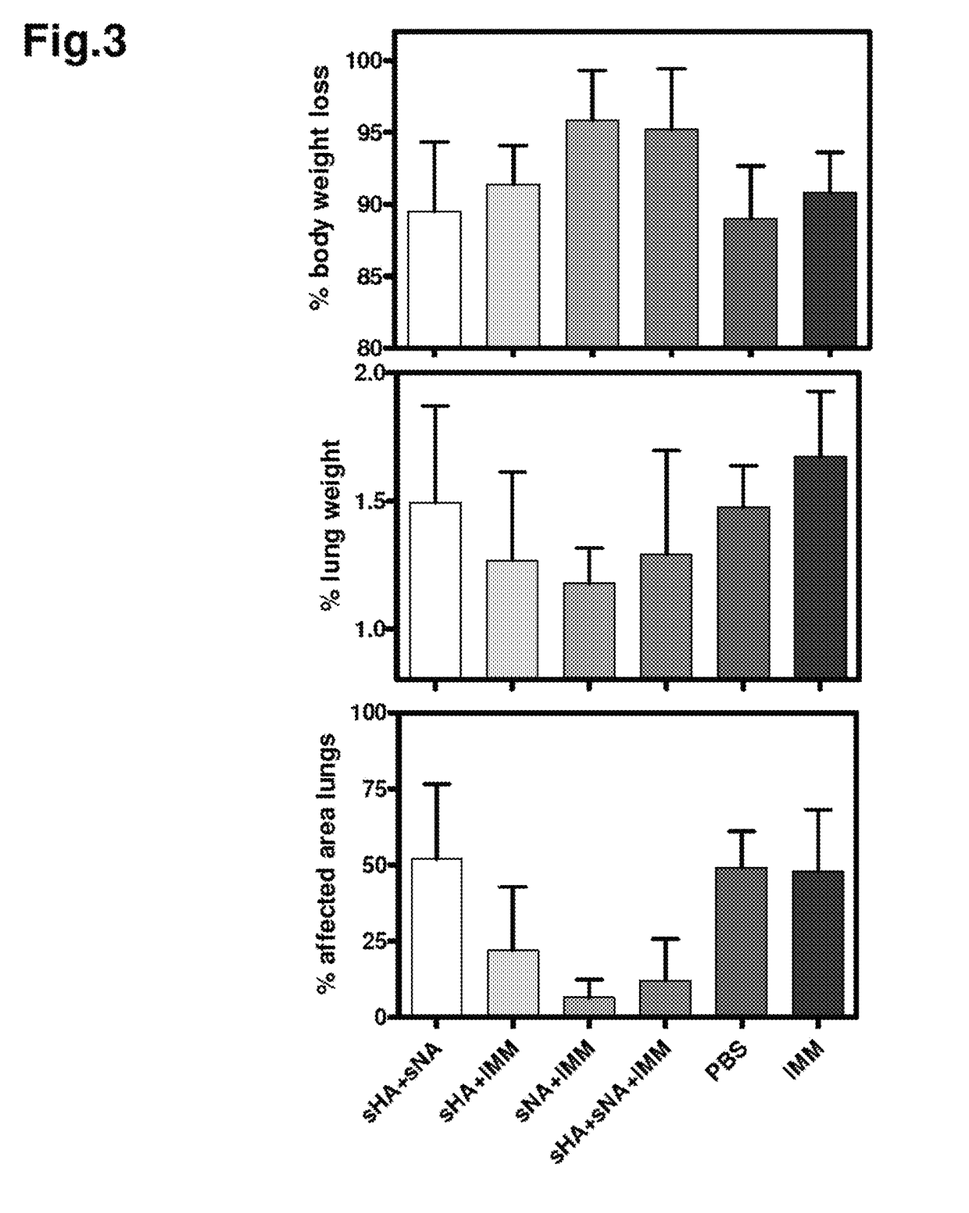
Figure 4:
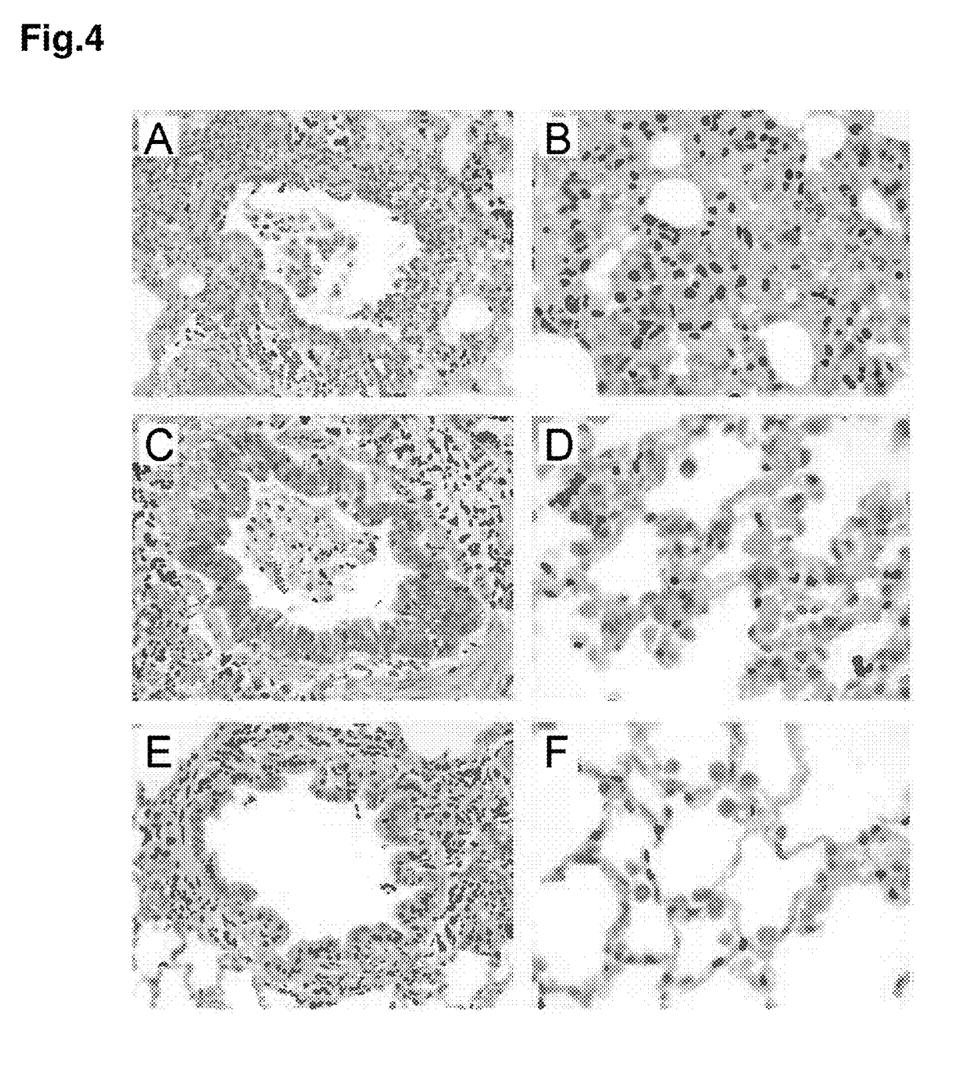
Figure 5:
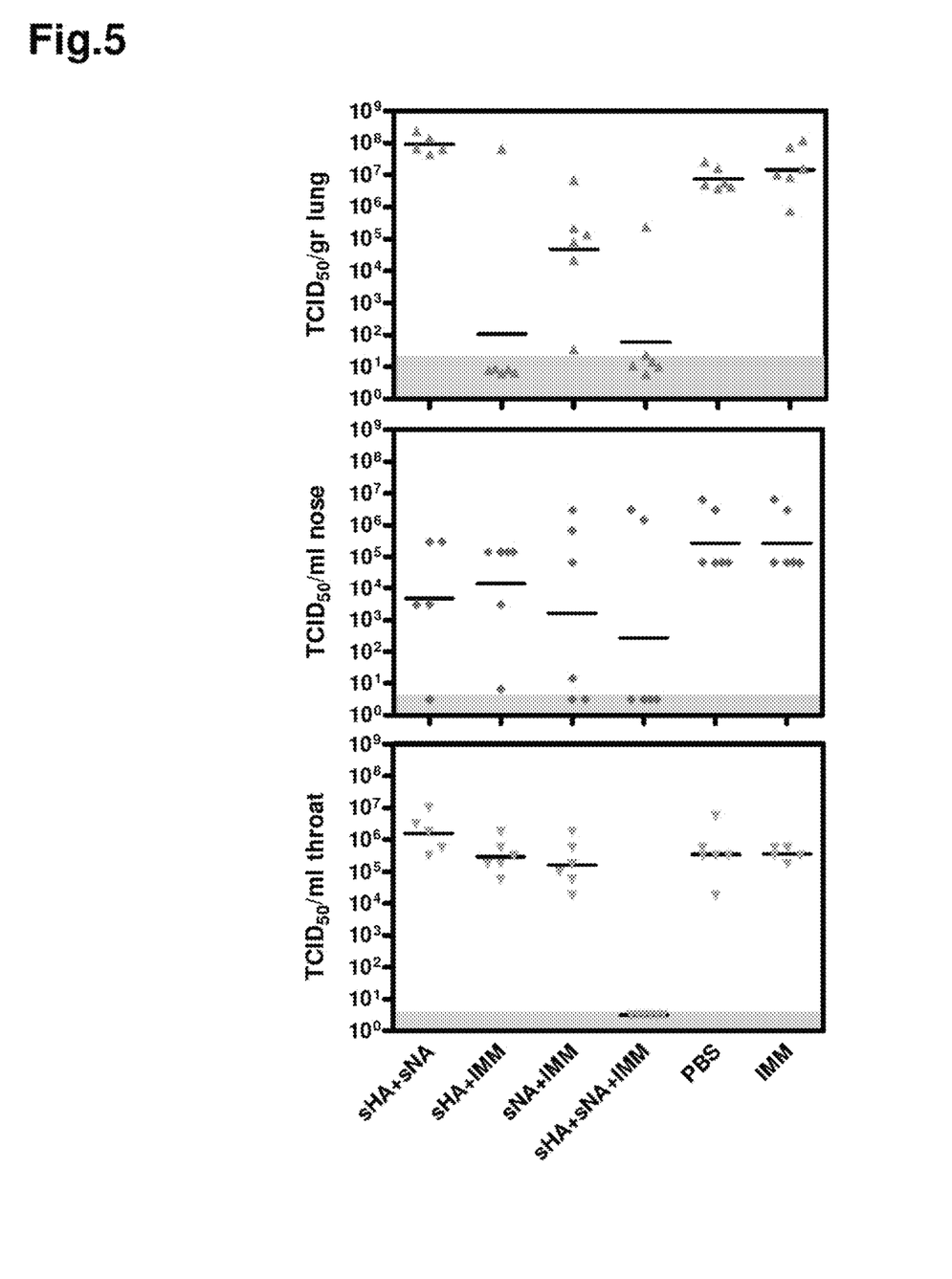

This was the case with the sera from both the sHA$_3$+IMM and the sHA$_3$+sNA$_4$$^+$IMM vaccinated animals. Consistent with the earlier observed differences in HI activity against the homologous virus (FIG. 2), the levels of cross-reactivity were markedly higher with the sera from ferrets immunised with sHA$_3$+sNA$_4$+IMM than with those from sHA$_3$+IMM immunised animals, confirming again the enhancing effect of the sNA$_4$ antigen. HI titers against each strain were detected in control sera of ferrets infected with the homologous influenza A/H1N1 virus (data not shown).

Figure 6:
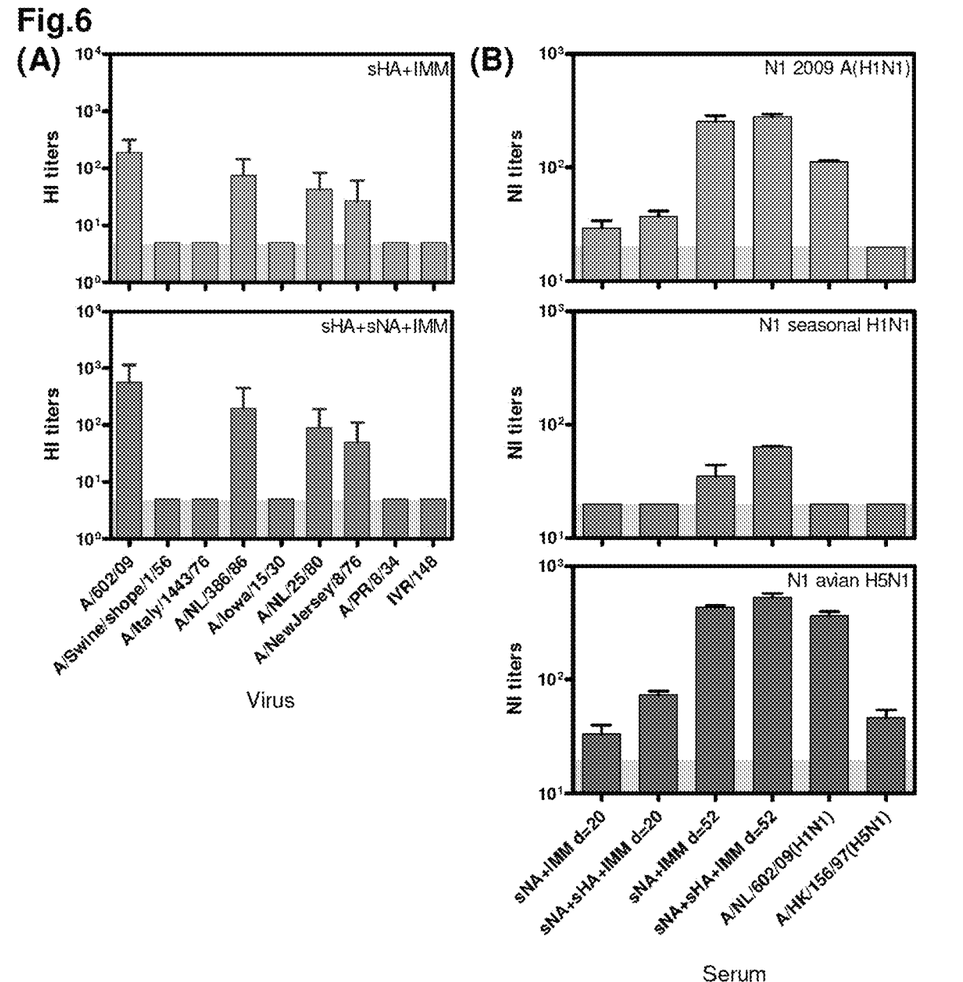

To investigate the cross-reactivity of the NA antibodies we produced sNA$_4$ glycoprotein complexes of two other N1 influenza viruses, the human H1N1 strain A/Kentucky/UR06-0258/2007 and the avian H5N1 strain A/turkey/Turkey/1/2005. When tested in our NI assay there was a strong neuraminidase inhibiting activity with the pooled sera of the sNA$_4$+IMM and sHA$_3$+sNA$_4$+IMM immunised animals against the avian H$_5$N$_1$ virus sNA$_4$ protein while some inhibition of the seasonal H1N1 virus sNA$_4$ protein was observed (FIG. 6B). Of note, a control serum derived from a H5N1 virus infected chicken tested negative against both human H1N1 virus sNA$_4$ proteins.

REFERENCES 1. who.int
2. Johansson, B. E., D. J. Bucher, and E. D. Kilbourne, Purified influenza virus hemagglutinin and neuraminidase are equivalent in stimulation of antibody response but induce contrasting types of immunity to infection. J Virol, 1989. 63(3): p. 1239-46.
3. Sylte, M. J. and D. L. Suarez, Influenza neuraminidase as a vaccine antigen. Curr Top Microbiol Immunol, 2009. 333: p. 227-41.
4. Johansson, B. E., B. Grajower, and E. D. Kilbourne, Infection-permissive immunisation with influenza virus neuraminidase prevents weight loss in infected mice. Vaccine, 1993. 11(10): p. 1037-9.
5. Chen, Z., et al., Enhanced protection against a lethal influenza virus challenge by immunisation with both hemagglutinin- and neuraminidase-expressing DNAs. Vaccine, 1999. 17(7-8): p. 653-9.
6. Deroo, T., W. M. Jou, and W. Fiers, Recombinant neuraminidase vaccine protects against lethal influenza. Vaccine, 1996. 14(6): p. 561-9.
7. Sandbulte, M. R., et al., Cross-reactive neuraminidase antibodies afford partial protection against H5N1 in mice and are present in unexposed humans. PLoS Med, 2007. 4(2): p. e59.
8. Schulman, J. L., M. Khakpour, and E. D. Kilbourne, Protective effects of specific immunity to viral neuraminidase on influenza virus infection of mice. J Virol, 1968. 2(8): p. 778-86.
9. Johansson, B. E., Immunisation with influenza A virus hemagglutinin and neuraminidase produced in recombinant bacula virus results in a balanced and broadened immune response superior to conventional vaccine. Vaccine, 1999. 17(15-16): p. 2073-80.
10. Johansson, B. E. and E D. Kilbourne, Dissociation of influenza virus hemagglutinin and neuraminidase eliminates their intravirionic antigenic competition. J Virol, 1993. 67(10): p. 5721-3.
11. Webster, R. G., W. G. Layer, and E. D. Kilbourne, Reactions of antibodies with surface antigens of influenza virus. J Gen Virol, 1968. 3(3): p. 315-26.
12. Johansson, B. E., T. M. Moran, and E. D. Kilbourne, Antigen-presenting B cells and helper T cells cooperatively mediate intravirionic antigenic competition between influenza A virus surface glycoproteins. Proc Natl Acad Sci USA, 1987. 84(19): p. 6869-73.
13. Powers, D. C., E. D. Kilbourne, and B. E. Johansson, Neuraminidase-specific antibody responses to inactivated influenza virus vaccine in young and elderly adults. Clin Diagn Lab Immunol, 1996. 3(5): p. 511-6.
14. Johansson, B. E., B. A. Pokorny, and VA Tiso, Supplementation of conventional trivalent influenza vaccine with purified viral N1 and N2 neuraminidases induces a balanced immune response without antigenic competition. Vaccine, 2002. 20(11-12): p. 1670-4.
15. Munster, V. J., et al., Pathogenesis and transmission of swine-origin 2009 A(H1N1) influenza virus in ferrets. Science, 2009. 325(5939): p. 481-3.
16. Rimmelzwaan, G. F., et al., Comparison of RNA hybridization, hemagglutination assay, titration of infectious virus and immunofluorescence as methods for monitoring influenza virus replication in vitro. J Virol Methods, 1998. 74(1): p. 57-66.
17. Li, W., et al., Angiotensin-converting enzyme 2 is a functional receptor for the SARS corona virus. Nature, 2003. 426(6965): p. 450-4.
18. Harbury, P. B., et al., A switch between two-, three-, and four-stranded coiled coils in GCN4 leucine zipper mutants. Science, 1993. 262(5138): p. 1401-7.
19. Cornelissen, L. A., et al., A single immunisation with soluble recombinant trimeric hemagglutinin protects chickens against highly pathogenic avian influenza virus H5N1. PLoS One. 5(5): p. e10645.
20. de Vries, R. P., et al., The influenza A virus hemagglutinin glycosylation state affects receptor-binding specificity. Virology. 403(1): p. 17-25.
21. van den Brand, J. M., et al., Severity of pneumonia due to new H1N1 influenza virus in ferrets is intermediate between that due to seasonal H1N1 virus and highly pathogenic avian influenza H5N1 virus. J Infect Dis. 201 (7): p. 993-9.
22. Del Giudice, G., et al., Seasonal influenza vaccine provides priming for A/H1N1 immunisation. Sci Transl Med, 2009. 1 (12): p. 12re1.
23. Palmer D, D W., Coleman M, Schild G, Haemagglutination inhibition test. Advanced laboratory techniques for 24. Frank, A. L., et al., Microneutralisation test for influenza A and B and parainfluenza 1 and 2 viruses that uses continuous cell lines and fresh serum enhancement. J Clin Microbiol, 1980. 12(3): p. 426-32.
25. de Jong, J. C., et al., Antigenic and molecular heterogeneity in recent swine influenza A(H1N1) virus isolates with possible implications for vaccination policy. Vaccine, 2001. 19(31): p. 4452-64.
26. Lambre, C. R., et al., An enzyme-linked lectin assay for sialidase. Clin Chim Acta, 1991. 198(3): p. 183-93.
27. Karber, G., Beitrag zur kollektiven behandlung pharmakologischer reihenversuche Exp. Pathol. Pharmakol., 1931. 162: p. 480-483.
28. Kilbourne, E D., Influenza, Plenum Publishing, New York (1987) pp. 164-5. 1987.
29. Kendal, A. P., F. M. Bozeman, and F. A. Ennis, Further studies of the neuraminidase content of inactivated influenza vaccines and the neuraminidase antibody responses after vaccination of immunologically primed and unprimed populations. Infect Immun, 1980. 29(3): p. 966-71.

The invention claimed is:

1. Composition comprising at least one ISCOM matrix and at least one isolated ectodomain from at least one hemagglutinin domain and at least one isolated ectodomain from at least one neuraminidase domain from one or more influenza virus, wherein the ectodomains represent ectodomains isolated from the influenza virus, the isolated ectodomains being isolated from the rest of the hemagglutinin and neuraminidase proteins; wherein the ectodomains are present in the composition at a ratio of neuraminidase ectodomain to hemagglutinin ectodomain that is greater than that of wild type influenza virus; and
wherein the at least one ISCOM matrix comprises at least one saponin and at least one lipid.

2. The composition according to claim 1, wherein one or more of the isolated ectodomains from at least one hemagglutinin domain and one or more of the isolated ectodomains from at least one neuraminidase domain are presented as hybrid proteins comprising at least one protein or portion thereof not of influenza virus.

3. The composition according to claim 1, wherein one or more of the isolated ectodomains from at least one hemagglutinin domain and one or more of the isolated ectodomains from at least one neuraminidase domain are a head domain.

4. The composition according to claim 1, wherein the influenza virus is chosen from a sub serotype of influenza from HxNy, wherein x is 1-16 and y is 1-9.

5. The composition according to claim 4, wherein the influenza virus is chosen from the group consisting of 1918 H1N1 influenza virus (A/South Carolina/1/18), 2004 H5N1 influenza virus (A/Vietnam/1203/04), H1N1 influenza virus (A/California/07/2009), H1N1 influenza virus (A/California/04/2009), H1N1 influenza virus (A/California/09/2009), H1N1 influenza virus (A/Kentucky/UR06-0258/2007), and H5N1 influenza virus (A/turkey/Turkey/1/2005).

6. The composition according to claim 1, wherein the composition comprises 1-5 ectodomains from at least one hemagglutinin domain and 1-5 head domains from at least one neuraminidase domain.

7. The composition according to claim 6, wherein the at least one hemagglutinin ectodomain is chosen from the trimeric HA ectodomain (a.a. 17-522) of the H1N1 influenza virus (A/California/09/2009).

8. The composition according to claim 6, wherein the at least one neuraminidase head domain is chosen from the tetrameric NA head domain (a.a. 75-469) of the H1N1 influenza virus (A/California/09/2009).

9. The composition according to claim 1, further comprising at least one of an additive, an excipient, and a further adjuvant.

10. A composition according to claim 1 for use as an immune stimulating medicine, an immune modulating pharmaceutical, or a vaccine against influenza for a vertebrate.

11. The composition according to claim 10, wherein the vertebrate is selected from the group consisting of human, cat, dog, horse, bird, cattle, bovine species, swine, sheep, goat, ferret, and mink.

12. A kit comprising at least two compartments, wherein one compartment comprises a composition comprising at least one ISCOM matrix and at least one isolated ectodomain from at least one hemagglutinin domain and at least one isolated ectodomain from at least one neuraminidase domain from one or more influenza virus and the other compartment comprises instructions for use, wherein the ectodomains represent ectodomains isolated from the influenza virus, the isolated ectodomains being isolated from the rest of the hemagglutinin and neuraminidase proteins, wherein the ectodomains are present in the composition at a ratio of neuraminidase ectodomain to hemagglutinin ectodomain that is greater than that of wild type influenza virus; and
wherein the at least one ISCOM matrix comprises at least one saponin and at least one lipid.

13. The composition of claim 1 wherein the ISCOM matrix comprises separate ISCOM matrix particles containing Fraction A and Fraction C.

14. The composition of claim 13 wherein the ISCOM matrix comprises from 5% to 50% (w/w) Fraction C ISCOM matrix particles with the remainder Fraction A ISCOM matrix particles.

15. The composition according to claim 13 wherein the ISCOM matrix comprises up to 30% (w/w) Fraction C ISCOM matrix particles with the remainder Fraction A ISCOM matrix particles.

16. The composition according to claim 14 wherein the ISCOM matrix comprises 15% (w/w) Fraction C ISCOM matrix particles and 85% Fraction A ISCOM matrix particles.

17. The kit of claim 12 wherein the ISCOM matrix comprises separate ISCOM matrix particles containing Fraction A and Fraction C.

18. The kit of claim 17 wherein the ISCOM matrix comprises from 5% to 50% (w/w) Fraction C ISCOM matrix particles with the remainder Fraction A ISCOM matrix particles.

19. The kit according to claim 17 wherein the ISCOM matrix comprises up to 30% (w/w) Fraction C ISCOM matrix particles with the remainder Fraction A ISCOM matrix particles.

20. The kit according to claim 18 wherein the ISCOM matrix comprises 15% (w/w) Fraction C ISCOM matrix particles and 85% Fraction A ISCOM matrix particles.

* * * * *